United States Patent
Rigg et al.

(10) Patent No.: US 10,702,475 B2
(45) Date of Patent: Jul. 7, 2020

(54) LIPOSOME CONTAINING COMPOSITIONS AND THEIR USE IN PERSONAL CARE AND FOOD PRODUCTS

(71) Applicants: Richard Rigg, Richmond Hill, NY (US); Imani Rigg, Springfiled Gardens, NY (US)

(72) Inventors: Richard Rigg, Richmond Hill, NY (US); Imani Rigg, Springfiled Gardens, NY (US)

(*) Notice: Subject to any disclaimer, the term of this patent is extended or adjusted under 35 U.S.C. 154(b) by 54 days.

(21) Appl. No.: 16/117,707

(22) Filed: Aug. 30, 2018

(65) Prior Publication Data

US 2019/0070114 A1 Mar. 7, 2019

Related U.S. Application Data

(60) Provisional application No. 62/554,047, filed on Sep. 5, 2017.

(51) Int. Cl.

| | |
|---|---|
| *A61K 9/127* | (2006.01) |
| *A61K 47/06* | (2006.01) |
| *A61K 8/891* | (2006.01) |
| *A61K 47/34* | (2017.01) |
| *A61K 47/14* | (2017.01) |
| *A61K 47/24* | (2006.01) |
| *A61K 47/36* | (2006.01) |
| *A61K 8/368* | (2006.01) |
| *A61K 47/20* | (2006.01) |
| *A61K 9/14* | (2006.01) |
| *A61K 47/38* | (2006.01) |
| *A61K 8/39* | (2006.01) |
| *A61K 47/18* | (2017.01) |
| *A61K 8/14* | (2006.01) |
| *A61K 47/10* | (2017.01) |
| *A61Q 5/12* | (2006.01) |
| *A61Q 19/00* | (2006.01) |
| *A61K 8/67* | (2006.01) |

(52) U.S. Cl.
CPC .............. *A61K 9/1272* (2013.01); *A61K 8/14* (2013.01); *A61K 8/368* (2013.01); *A61K 8/39* (2013.01); *A61K 8/671* (2013.01); *A61K 8/891* (2013.01); *A61K 9/1277* (2013.01); *A61K 9/14* (2013.01); *A61K 47/06* (2013.01); *A61K 47/10* (2013.01); *A61K 47/14* (2013.01); *A61K 47/186* (2013.01); *A61K 47/20* (2013.01); *A61K 47/24* (2013.01); *A61K 47/34* (2013.01); *A61K 47/36* (2013.01); *A61K 47/38* (2013.01); *A61Q 5/12* (2013.01); *A61Q 19/00* (2013.01)

(58) Field of Classification Search
CPC .......... A61K 9/1272; A61K 8/39; A61K 9/14; A61K 8/14
See application file for complete search history.

(56) References Cited

U.S. PATENT DOCUMENTS

| | | | | |
|---|---|---|---|---|
| 5,045,337 | A | * | 9/1991 | El-Nokaly ........... A23D 7/0053 426/601 |
| 5,085,857 | A | | 2/1992 | Reid et al. |
| 5,171,577 | A | * | 12/1992 | Griat ..................... A61K 8/046 424/450 |
| 5,720,973 | A | | 2/1998 | Rosenberg et al. |
| 5,849,941 | A | | 12/1998 | Rosenberg et al. |
| 6,383,471 | B1 | | 5/2002 | Chen et al. |
| 6,495,596 | B1 | | 12/2002 | Keller et al. |
| 6,610,322 | B1 | | 8/2003 | Keller et al. |
| 6,958,160 | B1 | | 10/2005 | Keller et al. |
| 6,979,440 | B2 | | 12/2005 | Shefer et al. |
| 6,998,421 | B2 | | 2/2006 | Keller et al. |
| 7,150,883 | B2 | | 12/2006 | Keller et al. |
| 7,718,190 | B2 | | 5/2010 | Keller et al. |
| 2006/0240049 | A1 | | 10/2006 | De Spiegeleer et al. |
| 2007/0110731 | A1 | * | 5/2007 | Riley .................... A61K 31/728 424/93.7 |
| 2012/0052042 | A1 | * | 3/2012 | Ladet ..................... A61K 47/34 424/78.24 |
| 2014/0227217 | A1 | * | 8/2014 | Matsuzawa ............ A61K 8/365 424/76.1 |
| 2016/0128964 | A1 | | 5/2016 | Arvidsson et al. |
| 2016/0184228 | A1 | * | 6/2016 | Morrison .............. A61K 9/1272 424/450 |
| 2017/0143604 | A1 | * | 5/2017 | Idkowiak-Baldys .... A61K 8/64 |

OTHER PUBLICATIONS

Mansour, M., et al in Colloids and Surfaces B: Biointerfaces. 156, pp. 44-54, 2017.*
Yamaguchi, S,m et ak ub J. Oleo Sci., 2016, vol. 65, (3) pp. 201-206.*
Abdelkader et al b Drug Delv. Mar. 21, 2014, (2), pp. 87-100.*
SALACOS(R) PG-18; Polyglyceryl-10 Dioleate; Aug. 22, 2017.

* cited by examiner

*Primary Examiner* — Rachael E Bredefeld
(74) *Attorney, Agent, or Firm* — Milton L. Honig

(57) ABSTRACT

A liposome is provided with liposome structuring amounts of polyglyceryl-10 dioleate and polyglyceryl-10 dilinoleate. Further, a liposome composition is described having polyglyceryl-10 dioleate and polyglyceryl-10 dilinoleate and an active material delivering consumer benefits incorporated into a lipid or aqueous phase of the liposome and an aqueous carrier suspending the liposomes therein. Finally, a liposome composition is provided including polyglyceryl-10 diacyl surfactants and a water soluble cationic material held within an interior aqueous medium of the liposome effective to retain the liposome on a substrate even subsequent to more than one aqueous rinse treatment.

14 Claims, No Drawings

LIPOSOME CONTAINING COMPOSITIONS AND THEIR USE IN PERSONAL CARE AND FOOD PRODUCTS

BACKGROUND OF THE INVENTION

Field of the Invention

The invention relates to non-solid liposomal particles for use in personal care and food products.

The Related Art

Liposomes are structures formed by polar lipid molecules or by amphiphilic molecules, each having a polar head and a long hydrophobic tail. The liposomes can be structured as liquid particles. These particles comprise an outer shell of one or more membrane-type bilayers of molecules concentrically arranged around a hollow interior referred to as a vacuole. Interiors of vacuoles can serve as storage compartments for active agents. The outer shell or layer normally orients the polar heads facing outwardly of the liposome. The hydrophobic tails are dangled inwardly. Examples of polar heads are carboxylic, polyol and phosphate functional groups. Tails often are $C_{12}$ to $C_{30}$ hydrocarbyl chains, particularly palmityl, oleoyl and stearyl groups. If there are multiple liposomal layers, orientation is reversed in alternate layers. Lipid tails of one layer will here intermingle with tails of the next, and the polar heads of one layer abut those of a neighbor.

Active agents stored in the interior of the liposome in the lipid or aqueous portion are sheltered from alien media by the surrounding membrane of amphiphilic molecules. Further, typically the liposomes are dispersed in an aqueous medium or polar solvent medium.

U.S. Pat. No. 7,150,883 (Keller et al) and related documents U.S. Pat. Nos. 6,958,160 and 6,610,322, disclose lipid compositions based on diacylglycerol-PEG compounds. Liposomes are formed from the lipid compositions. Therapeutic agents may be delivered transdermally, intravenously or otherwise via the liposomes to the human body. Newer agents requiring liposomal delivery are continuously being discovered. Known liposomal forming surfactants are not always capable of structuring liposomes with the newer agents. An important aspect of the present invention is to identify more robust surfactants to structure liposomes. We have found that the window of operative function is a narrow one.

SUMMARY OF THE INVENTION

A liposome is provided including liposome structuring amounts of polyglyceryl-10 dioleate and polyglyceryl-10 dilinoleate in a weight ratio of 300:1 to 5:1.

Further, a composition is provided which includes:
a) liposomes having:
  (i) liposome structuring amounts of polyglyceryl-10 dioleate and polyglyceryl-10 dilinoleate in a weight ratio of 300:1 to 5:1; and
  (ii) active materials delivering consumer benefits incorporated into a lipid or aqueous phase of the liposome; and
b) an aqueous carrier suspending the liposomes therein.

Still further, a liposome composition is provided with liposome structuring amounts of polyglyceryl-10 diacyl surfactants, acyl units forming the surfactants having from 12 to 20 carbons; and a water soluble cationic material held within an interior aqueous medium of the liposome present in an effective amount to retain the liposome on a substrate even subsequent to more than one aqueous rinse treatment.

DETAILED DESCRIPTION OF THE INVENTION

Now we have found certain polyglyceryl substances which readily form liposomes. These are polyglyceryl-10 diacyl substances. The acyl units will have from 12 to 20 carbons per chain, particularly from 12 to 18 carbons per chain. Total percentage of polyglyceryl-10 diacyl substances within the liposome may range from 0.1 to 50, generally from 0.5 to 20, and especially from 1 to 3% by weight of the liposome.

By the term "polyglyceryl-10" is meant to include polyglyceryl-8, polyglyceryl-10 and polyglyceryl-12, with proviso that from 50 to 100, generally from 70 to 95, and more generally from 80 to 90 weight % of the polyglyceryl is polyglyceryl-10 in actuality without lower or higher levels of glycerol monomer units.

In one aspect, we have found liposome compositions with liposome structuring amounts of polyglyceryl-10 diacyl surfactants when incorporating a water soluble cationic material within an Interior aqueous medium of the liposome results in the liposome becoming resistant to otherwise easy wash off from skin and hair.

In another aspect, we have found that a combination of polyglyceryl-10 dioleate and polyglyceryl-10 dilinoleate in a weight ratio of 300:1 to 5:1, usually from 100:1 to 10:1, especially 100:8 to 100:4, provides excellent stability to liposome formations and enhances deposition of actives.

In still another aspect, liposomes described herein may have a Dynamic Light Scattering (DLS) value ranging from 1 to 1000, preferably from 5 to 250, and optimally from 100 to 200 nm. Suitable for DLS measurement is a Zetasizer Nano Range instrument available commercially from Malvern Panalytics Ltd, United Kingdom. The instrument has capability to measure size and size distributions of dispersed or dissolved molecules in the submicron region.

Active agents may be incorporated into the liposomes for deposit on substrates. These active agents may be selected from the group consisting of fragrances, flavors, sunscreens, hair conditioners (e.g. cationic materials), vitamins, antioxidants, colorants, preservatives and emollients. Further useful active agents for skin treatment include alpha and beta hydroxy acids, retinoids, proteins, peptides, sulphur, plant actives, benzoyl peroxide, whitening agents, exfoliating agents, moisturizers and combinations thereof.

The relative weight ratio of total polyglyceryl-10 diacyl substances to active agent may range from 1:200 to 200:1, preferably from 1:10 to 10:1, and most particularly from 1:2 to 2:1.

Among the cationic materials useful herein are monomeric and polymeric cationic materials (alternatively referred to as 'quats'). Monomeric mono-, di-, and tri-alkyl or aryl quats are exemplified by cetyltrimethylammonium chloride, cetylpyridinium chloride, behenyltrimethylammonium methosulfate, benzyltrimethylammonium chloride, and oleoylmonomethyldihydrogenammonium chloride.

Polyquaternium is the International Nomenclature for Cosmetic Ingredients (INCI) designation for several polycationic polymers that are used in the personal care industry. Polyquaternium is a neologism used to emphasize the presence of quaternary ammonium centers in the polymer. INCI has approved at least 37 different polymers under the polyquaternium designation. Different polymers are distinguished by the numerical value that follows the word "polyquaternium". Polyquaternium-5, polyquaternium-7, and polyquaternium-47 are three examples, each a chemically different type of polymer. The numbers are assigned in the order in which they are registered rather than because of their chemical structure.

| List of Polyquaterniums | |
|---|---|
| Polyquaternium | Chemical Identity |
| Polyquaternium-1 | Ethanol,2,2',2''-nitrilotris-, polymer with 1,4-dichloro-2-butene and N,N,N',N'-tetramethyl-2-butene-1,4-diamine |
| Polyquaternium-2 | Poly[bis(2-chloroethyl) ether-alt-1,3-bis[3-(dimethylamino)propyl]urea] |
| Polyquaternium-4 | Hydroxyethyl cellulose dimethyl diallylammonium chloride copolymer; Diallyldimethylammonium chloride-hydroxyethyl cellulose copolymer |
| Polyquaternium-5 | Copolymer of acrylamide and quaternized dimethylammoniumethyl methacrylate |
| Polyquaternium-6 | Poly(diallyldimethylammonium chloride) |
| Polyquaternium-7 | Copolymer of acrylamide and diallyldimethylammonium chloride |
| Polyquaternium-8 | Copolymer of methyl and stearyl dimethylaminoethyl ester of methacrylic acid, quaternized with dimethylsulphate |
| Polyquaternium-9 | Homopolymer of N,N-(dimethylamino)ethyl ester of methacrylic acid, quaternized with bromomethane |
| Polyquaternium-10 | Quaternized hydroxyethyl cellulose |
| Polyquaternium-11 | Copolymer of vinylpyrrolidone and quaternized dimethylaminoethyl methacrylate |
| Polyquaternium-12 | Ethyl methacrylate/abietyl methacrylate/diethylaminoethyl methacrylate copolymer quaternized with dimethyl sulfate |
| Polyquaternium-13 | Ethyl methacrylate/oleyl methacrylate/diethylaminoethyl methacrylate copolymer quaternized with dimethyl sulfate |
| Polyquaternium-14 | Trimethylaminoethylmethacrylate homopolymer |
| Polyquaternium-15 | Acrylamide-dimethylaminoethyl methacrylate methyl chloride copolymer |
| Polyquaternium-16 | Copolymer of vinylpyrrolidone and quaternized vinylimidazole |
| Polyquaternium-17 | Adipic acid, dimethylaminopropylamine and dichloroethylether copolymer |
| Polyquaternium-18 | Azelaic acid, dimethylaminopropylamine and dichloroethylether copolymer |
| Polyquaternium-19 | Copolymer of polyvinyl alcohol and 2,3-epoxypropylamine |
| Polyquaternium-20 | Copolymer of polyvinyl octadecyl ether and 2,3-epoxypropylamine |
| Polyquaternium-22 | Copolymer of acrylic acid and diallyldimethylammonium Chloride |
| Polyquaternium-24 | Quaternary ammonium salt of hydroxyethyl cellulose reacted with a lauryl dimethyl ammonium substituted epoxide. |
| Polyquaternium-27 | Block copolymer of Polyquaternium-2 and Polyquaternium-17 |
| Polyquaternium-28 | Copolymer of vinylpyrrolidone and methacrylamidopropyl trimethylammonium |
| Polyquaternium-29 | Chitosan modified with propylene oxide and quaternized with epichlorohydrin |
| Polyquaternium-30 | Ethanaminium, N-(carboxymethyl)-N,N-dimethyl-2-[(2-methyl-1-oxo-2-propen-1-yl)oxy]-, inner salt, polymer with methyl 2-methyl-2-propenoate |
| Polyquaternium-31 | N,N-dimethylaminopropyl-N-acrylamidine quaternized with diethylsulfate bound to a block of polyacrylonitrile |
| Polyquaternium-32 | Poly(acrylamide 2-methacryloxyethyltrimethyl ammonium chloride) |
| Polyquaternium-33 | Copolymer of trimethylaminoethylacrylate salt and acrylamide |
| Polyquaternium-34 | Copolymer of 1,3-dibromopropane and N,N-diethyl-N',N'-dimethyl-1,3-propanediamine |
| Polyquaternium-35 | Methosulphate of the copolymer of methacryloyloxyethyltrimethylammonium and of methacryloyloxyethyldimethylacetylammonium |
| Polyquaternium-36 | Copolymer of N,N-dimethylaminoethylmethacrylate and butylmethacrylate, quaternized with dimethylsulphate |
| Polyquaternium-37 | Poly(2-methacryloxyethyltrimethylammonium chloride) |
| Polyquaternium-39 | Terpolymer of acrylic acid, acrylamide and diallyldimethylammonium Chloride |
| Polyquaternium-42 | Poly[oxyethylene(dimethylimino)ethylene (dimethylimino)ethylene dichloride] |
| Polyquaternium-43 | Copolymer of acrylamide, acrylamidopropyltrimonium chloride, 2-amidopropylacrylamide sulfonate and dimethylaminopropylamine |
| Polyquaternium-44 | 3-Methyl-1-vinylimidazolium methyl sulfate-N-vinylpyrrolidone copolymer |
| Polyquaternium-45 | Copolymer of (N-methyl-N-ethoxyglycine)methacrylate and N,N-dimethylaminoethylmethacrylate, quaternized with dimethyl sulphate |

-continued

| List of Polyquaterniums | |
|---|---|
| Polyquaternium | Chemical Identity |
| Polyquaternium-46 | Terpolymer of vinylcaprolactam, vinylpyrrolidone, and quaternized vinylimidazole |
| Polyquaternium-47 | Terpolymer of acrylic acid, methacrylamidopropyl trimethylammonium chloride, and methyl acrylate |

Of particular use herein are saccharide based quats such as guar hydroxypropyltrimethylammonium chloride with variants sold by Novacare under the trademark Jaguar®, hydroxypropyltrimethylammonium hydrolyzed wheat protein sold by Croda International, and hydroxypropyltrimethylammonium honey sold under the mark Honeyquat®.

Amounts of the cationic material in the liposomes may range from 0.00001 to 30%, normally from 0.001 to 10%, and particularly from 0.01 to 1% by weight. Advantageously, the relative weight ratio of polyglyceryl-10 diacyl substance to cationic material may range from 1:100 to 100:1, preferably from 1:10 to 10:1, and most particularly from 1:2 to 2:1.

Fragrances are ideally suited as active agents for delivery to substrates via the liposomes disclosed herein.

Representative fragrance oils having a boiling point of below 250° C. at 1 bar pressure include the following materials: anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde, phenyl acetaldehyde, anisic aldehyde, benzyl acetone, ethyl-2-methyl butyrate, damascenone, damascone alpha, damascone beta, for acetate, frutene, fructone, herbavert, methyl isobutenyl tetrahydropyran, iso propyl quinoline, 2,6-nonadien-1-ol, 2-methoxy-3-(2-methylpropyl)-pyrazine, methyl octine carbonate, cyclogalbanate, gamma nonalactone, cis 1,3-oxathiane-2-methyl-4-propyl, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaidehyde dimethyl acetal, phenyl propyl alcohol, prenyl acetate, tetrahydrolinalool, verdox, and cis-3-hexenyl acetate.

Representative fragrance oils having a boiling point at 1 bar pressure of at least 250° C. include:— ethyl methyl phenyl glycidate, ethyl vanillin, heliotropin, Indol, methyl anthranilate, vanillin, amyl salicylate, coumarin, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxy I phenyl butanone, 8-cyclohexadecen-1-one, oxocyclohexadecen-2-one/habanolide, florhydral, intreleven aldehyde eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate. The fragrances potentially employed herein ordinarily comprise a preformed blend, either extracted from natural products, or possibly created synthetically. Representatives of such preformed blends include oils from:— Bergamot, cedar atlas, cedar wood, clove, geranium, guaiac wood, jasmine, lavender, lemongrass, lily of the valley, lime, neroli, musk, orange blossom, patchouli, peach blossom, petitgrain or petotgrain, pimento, rose, rosemary, and thyme.

Another group of suitable fragrance components are the so-called 'aromatherapy' materials. These include many components also used in perfumery, including components of essential oils such as Clary Sage, Eucalyptus, Geranium, Lavender, Mace Extract, Neroli, Nutmeg, Spearmint, Sweet Violet Leaf and Valerian.

The most useful fragrances comprise at least two essential oils selected from aromatic essential oils including amyl salicylate, carvacrol, cymene, dihydroeugenol, eugenol, hexyl eugenol, hexyl salicylate, isoeugenol, methyl eugenol, methyl isoeugenol, methyl salicylate, tert butyl cresol, thymol, and vanillin; and non-aromatic essential oil terpenoid compounds including cedrene, cineole, citral (including geranial and neral), citronellal, citronellol, eucalyptol (also known as 1,8 cineole) paradihydrolinalool, dihydromyrcenol, farnesol, geraniol, hexyl cinnamaldehyde, hydroxycitronallol, hydroxycitronellal, isocitral, limonene, preferably d-limonene, linalool, longifolene, menthol, nerol, nerolidiol, pinene, e.g. α-pinene, phellendrene, terpinene, e.g. α-terpinene and γ-terpinene, terpineol, e.g. γ-terpineol and terpin-4-ol, and tetrahydromyrcenol. Particularly preferred are thymol, terpineol, eugenol and mixtures thereof.

Each fragrance component when present may be found in a concentration of between 0.0001 and 10% by weight of the liposome composition, but preferably at least 0.002%, or even at least 0.005% by weight of the liposomes.

Flavors that may be suitable include furanones, esters, aldehydes, hydrocarbons, lactones and combinations thereof. Furanones are represented by 4-methoxy-2,5-dimethyl-3(2H)-furanone, 4-hydroxy-2,5-dimethyl-3(2H)-furanone, 3-hydroxy-4,5-dimethyl-2(5H)-furanone, and combinations thereof. The ester may be ethyl-2-methypropanoate, ethyl butanoate, ethyl-2-methybutanoate, ethyl-3-methylbutanoate, and combinations thereof. The aldehydehyde can be (E)-3-hexenal, (Z)-3-hexenal, (E)-2-nonenal, (E,Z)-2,6-nonadienal, and combinations thereof. Representative hydrocarbons are myrcene, P-(Z)-ocimene, P-(E)-ocimene, 1-(E,Z)-undecatriene, 1,3,5,8-undecatetraene, and combinations thereof. Lactones useful herein include γ-octalactone, γ-decalactone, 5-decalactone, and combinations thereof. Flavors may also include cultivars such as ethyl-2-methypropanoate, ethyl butanoate, ethyl-2-methybutanoate, ethyl-3-methylbutanoate, 2-acetyl-1-pyrroline, 1-(E,Z)-undecatriene, 3-(methyithio)-propanal, phenylethyl alcohol, γ-octalactone, and combinations thereof.

Sunscreen actives used herein may be organic or Inorganic. They include both UVA and UVB protective ranges. Organic sunscreens will have at least one chromophoric group absorbing within the ultraviolet ranging from 290 to 400 nm. Chromophoric organic sunscreens may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane).

Particularly important sunscreen actives are: 2-ethylhexyl p-methoxycinnamate (available as Parsol MCX®), 4,4'-t-butyl methoxydibenzoylmethane (known commonly as Avobenzone, available as Parsol 1789®), octylsalicylate (available as Dermablock OS®), tetraphthalylidene dicamphor sulfonic acid (available as Mexoryl SX®), benzophenone-3 (Oxybenzone) and mixtures thereof.

Inorganic sunscreen actives are usually microfine particles of titanium dioxide and of zinc dioxide. "Microfine" is defined herein as average particle size ranging from 10 to 200 nm, usually from 20 to 100 nm.

Amounts of sunscreen active may range from 0.01 to 20%, usually from 0.5 to 15%, and often from 4 to 12% by weight of the liposomes.

Emollient active materials may be selected from triglyceride and synthetic esters, hydrocarbon oils, silicones, fatty alcohols, fatty acids and polyols. Amounts of the emollients may range anywhere from 0.1 to 30%, preferably between 1 and 15% by weight of the liposomes.

Illustrative of triglyceride esters are vegetable derived oils and waxes such as sunflowerseed oil, cottonseed oil, rapeseed oil, coconut oil, olive oil, soybean oil, safflowerrseed oil, aloe vera, beeswax, spermaceti wax, tribehenin wax and mixtures thereof. Suitable synthetic esters include behenyl neopentanoate, isononyl isonanonoate, isopropyl myristate and octyl stearate. Particularly useful are pentaerythritol, trimethylolpropane and neopentyl glycol esters of $C_1$-$C_{30}$ alcohols, sucrose polybehenate, sucrose polycottonseedate and mixtures thereof.

Emollient active materials include silicone oils which may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient active material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Hydrocarbon emollients include petrolatum, mineral oil, polybutene, polyisobutylene, polyisobutene, hydrogenated polyisobutene and $C_{11}$-$C_{13}$ isoparaffins, and mixtures thereof.

Fatty acid emollients are those having from 10 to 30 carbon atoms. Illustrative of this category are pelargonic, lauric, myristic, palmitic, stearic, isostearic, oleic, hydroxystearic and behenic acids.

Fatty alcohol emollients are those having from 10 to 30 carbon atoms. Illustrative are stearyl alcohol, lauryl alcohol, myristyl alcohol and cetyl alcohol.

Polyol emollients may include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof.

Water will be present in the liposomes in amounts ranging from 5 to 98%, preferably 20 to 70%, optimally from 35 to 60% by weight of the liposome. Preferably, water will be a deionized, sterilized or pasteurized liquid or can be heat treated or irradiated after having been mixed with other components of the composition. These treatments insure elimination of pathogenic microbes.

Consumer products into which the liposome compositions may be formulated into include shampoos and hair conditioners, body wash, toilet soap bars, toothpastes, mouthwashes, laundry detergents, fabric softeners, sunscreens, shaving creams, skin lotions and creams.

Except in the examples, or where otherwise explicitly indicated, all numbers in this description indicating amounts of material or conditions of reaction, physical properties of materials and/or use are to be understood as modified by the word "about." All amounts are by weight of the compositions, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Product" as used herein, is meant to include a formulated personal care composition for topical application to skin or hair of mammals, especially humans or for deposition onto textiles via laundering. "Product" also includes formulated food compositions.

Example 1

Herein is described a general process for the manufacture of liposome containing compositions typical of the present invention. Experiments 1-6 appearing in the Table below show the relative weight amounts of the components subject to processing.

| Phase | Ingredient | Ex 1 | Ex 2 | Ex 3 | Ex 4 | Ex 5 | Ex 6 |
|---|---|---|---|---|---|---|---|
| A | Liposome forming material (Polyglyceryl-10 Diacyl) | 33.0 | 20.0 | 20.0 | 25.0 | 5.0 | 1.0 |
| A | Oil soluble active (e.g. fragrance oils, sunscreens, emollients) | 33.0 | 40.0 | 30.0 | 5.0 | 5.0 | 1.0 |
| B | Water | 34.0 | 40.0 | 50.0 | 70.0 | 90.0 | 98.0 |

The components of Phase A are combined and vigorously mixed with a Caframo-type lightening agitator. If the Polyglyceryl-10 Diacyl lipid is a solid, heat is applied to melt and maintain temperature at the melting temperature of the lipid. Thereafter, Phase B is very slowly added to Phase A with further vigorous mixing in the Caframo fitted vessel. Mixing is continued until all of Phase B is added to Phase A. A liposomal composition is thereby produced.

The above composition may then be added below 50 C to a product formula requiring delivery of an active material displaying benefits to a target substrate.

Example 2

The present example describes a deposition study of a liposome delivering a fragrance benefit. In the Table below, the test formula is referred to as Ex 7.

| Phase | Ingredient | Ex 7 |
|---|---|---|
| A | Liposome forming material (Polyglyceryl-10 Dioleate and Polyglyceryl-10 Dilinoleate) | 20.0 |
| A | Fragrance oil | 20.0 |
| B | Cetrimonium Chloride/Water (70:30) | 10.0 |
| C | Water | 50.0 |

Formula Ex 7 was prepared by first warming the lipid phase A to 40 C with constant mixing utilizing a Caframo-type lightening mixer. An aqueous phase B was added slowly to phase A under the mixing conditions. Thereafter, phase C (water) was slowly added to the combined phases A/B to create a milky solution.

Example 3

A pair of Hair Conditioner bases having formulas Ex 8 and 9 were prepared and their components are listed in the Table below.

| Phase | Ingredient | Ex 8 | Ex 9 |
|---|---|---|---|
| A | Water | 89.0 | 93.0 |
| A | Behentrimonium Methosulfate (and) Cetearyl Alcohol | 6.0 | 6.0 |
| B | Ex7 (Fragrance within quat containing liposome) | 5.0 | — |
| B | Fragrance (not within any liposome) | — | 1.0 |

These formulas were prepared by first heating aqueous phase A at 85 C while stirring vigorously with a Caframo-type lightening stirrer until a homogeneous solution was formed. The resultant solution was cooled to 45 C and oil phase B was added slowly with mixing. Upon complete mixing, the liposome mixture was cooled to 35 C and thereby forming the hair conditioner base.

Example 4

This example relates to the application of hair conditioners (Ex 8 and 9) on hair tresses and the evaluation of fragrance delivery substantivity. The Ex 8 and 9 compositions in an amount of 3 grams each was added to a respective 6 grams of bleached blond hair tresses. The compositions were massaged and combed into the respective tresses. Both tresses were allowed to stand at room temperature for 2 minutes. They were then washed using warm water (about 35 C) and subsequently air dried for 24 hours.

Both tresses were fragrance evaluated (blind trial) by a panel of eight persons.

The panel evaluated the scent of each tress after 24 hrs, 72 hrs, 1 week and 2 weeks. Scent intensity was rated on a scale of 1-10 where a score of 10 is always the tress with the higher level of fragrance and the other tress is graded relative to the higher level. Results are reported in the Table below. It is evident that Ex 8 formulated with quat incorporated liposomes retained most of the scent even after 2 weeks. Ex 9 formulation with fragrance outside any liposome only imparted scent to the treated tress for hardly 1 week.

| Ex | 24 hr Score | 48 hr score | 1 week | 2 weeks |
|---|---|---|---|---|
| 8 | 10 | 10 | 10 | 10 |
| 9 | 10 | 8 | 5 | 1 |

Example 5

A study was conducted to determine penetration of a Vitamin E Acetate loaded liposome formed of Polyglyceryl-10 Dioleate/Polyglyceryl-10 Dilinoleate. The Table below outlines the results. It is evident that liposome formate delivered Vitamin E acetate in a rapid and effectual manner.

| Vitamin E (ug/cm2) | Time(Hours) |
|---|---|
| 0.00 | 0 |
| 20.00 | 2 |
| 25.00 | 4 |
| 27.50 | 8 |

Example 6

This Example Illustrates application of the liposome to a bodywash product. See the formulation outlined in the Table below.

| Component | Weight (%) |
|---|---|
| Petrolatum | 20 |
| Liposome (Polyglyceryl-10 Dioleate) | 10 |
| Sodium Laureth Sulfate | 10 |
| Cocamidopropyl Betaine | 8 |
| PEG-14M | 4 |
| Fragrance | 1 |
| Water | Balance to 100 |

Example 7

This Example illustrates application of the liposome to a sunscreen product. See the formulation outlined in the Table below.

| Component | Weight (%) |
|---|---|
| Glycerol | 20 |
| Stearyl Alcohol | 10 |
| Caprylyl Glycol | 7 |
| Xanthan Gum | 8 |
| Liposome (Polyglyceryl-10 Dioleate/Dilinoleate and oil phase with Oxybenzone, Octisalate, Avobenzone and Octocrylene) | 15 |
| Fragrance | 1 |
| Preservative | 1 |
| Water | Balance to 100 |

Example 8

This Example illustrates application of the liposome with a mouthwash product. See the formulation outlined in the Table below.

| Component | Weight (%) |
|---|---|
| Glycerol | 20 |
| Liposome (Polyglyceryl-10 Dioleate and Polyglyceryl-10 Dilinoleate) and Flavor in 10:3 ratio | 13 |
| Poloxamer 407 | 2 |
| Methyl Paraben | 0.3 |
| Propyl Paraben | 0.2 |
| Sodium Saccharin | 0.05 |
| Colorant | 0.05 |
| Water | Balance to 100 |

Example 9

A series of polyglyceryl ester surfactants were evaluated to identify those capable of structuring a liposome. Results are reported in the Table below. These reveal that liposome formation requires from 8 to 12 units of glycerol and a di-ester of C14-C18 fatty acid to establish a liposomal structure.

| O/W Emulsion-Forming | Liposome-Forming | W/O Emulsion-Forming |
|---|---|---|
| Polyglyceryl-10 Dicocoate | Polyglyceryl-10 Distearate | Polyglyceryl-10 Decaoleate |
| Polyglyceryl-10 Cocoate | Polyglyceryl-10 Dilinoleate | Polyglyceryl-10 Decahydroxystearate |
| Polyglyceryl-10 Caprylate | Polyglyceryl-10 Dipalmitate | Polyglyceryl-10 Decastearate |
| Polyglyceryl-10 Caprate | Polyglyceryl-8 Dioleate | Polyglyceryl-3 Distearate |
| Polyglyceryl-10 Caprate/Caprylate | Polyglyceryl-8 Dipalmitate | Polyglyceryl-3 Polyricinoleate |
| Polyglyceryl-10 Oleate | Polyglyceryl-12 Dioleate | Polyglyceryl-3 Distearate |
| Polyglyceryl-10 Mono/Dioleate | Polyglyceryl-10 Dioleate | |
| Polyglyceryl-4 Cocoate | Polyglyceryl-10 Dimyristate | |
| Polyglyceryl-6 Dicaprate | | |

There are numerous combinations for each category and the normal rule of HLB does not apply. For example, Polyglyceryl-10 Mono/Dioleate has a HLB value of 10-11 and forms O/W emulsions, while Polyglyceryl-10 Dioleate has the same HLB (10-11) but forms liposomes instead of an O/W.

Example 10

General Example 1: Oil and Water Soluble Active in a Single Liposome

| Phase | Ingredient | % |
|---|---|---|
| A | Polyglyceryl Diacyl ester | 10.0 |
| A | Oil soluble material (Actives: Retinoids, salicylic acid, etc.) | 10.0 |
| B | Water | 10.0 |
| B | Water soluble active | 10.0 |
| C | Water | 60.0 |

The general manufacturing process starts by stirring phase A with a Lightening mixer until components are homogeneous. Phase B is charged to a separate vessel and mixed until components therein are also homogeneous. Phase B is then slowly added to phase A under agitation with the Lightening mixer and mixing continued for 10 further minutes. Thereafter, phase C is added to the combined phases A/B forming a white milky solution.

Specific Example 1: Oil and Water Soluble Active in a Single Liposome

| Phase | Ingredient | % |
|---|---|---|
| A | Polyglyceryl-10 Dioleate/Polyglyceryl-10 Dilinoleate | 10.0 |
| A | Retinol | 1.0 |
| A | Caprylic/Capric Triglyceride | 9.0 |
| B | Water | 19.0 |
| B | Caffeine | 1.0 |
| C | Water | 60.0 |

The specific Example 2 manufacturing process was started by stirring phase A with a Lightening mixer until components were homogeneous. Phase B was charged to a separate vessel and mixed until components therein were also homogeneous. Phase B was then slowly added to phase A under agitation by the Lightening mixer and mixing was continued for 10 further minutes. Thereafter, phase C was added to the combined phases A/B forming a white milky solution.

Specific Example 2: Oil Soluble Active in a Liposome

| Phase | Ingredient | % |
|---|---|---|
| A | Polyglyceryl-10 Dioleate/Polyglyceryl-10 Dilinoleate | 10.0 |
| A | Salicylic Acid | 1.0 |
| A | C12-15 Alkyl Benzoate | 9.0 |
| B | Water | 20.0 |
| C | Water | 60.0 |

The specific oil soluble active Example 2 manufacturing process was started by stirring phase A with a Lightening mixer at 60° C. until a clear solution formed. Phase B was charged to a separate vessel and mixed until components therein were homogeneous. Phase B was then slowly added to phase A under agitation with the Lightening mixer and mixing was continued for 10 further minutes. Thereafter, phase C was added to the combined phases A/B forming a white milky solution.

Specific Example 3: Oil Soluble Active in a Liposome

| Phase | Ingredient | % |
|---|---|---|
| A | Polyglyceryl-10 Dipalmitate | 10.0 |
| A | Salicylic Acid | 1.0 |
| A | C12-15 Alkyl Benzoate | 9.0 |
| B | Water | 20.0 |
| C | Water | 60.0 |

The specific oil soluble active in a liposome Example 3 manufacturing process was started by stirring phase A with a Lightening mixer at 60° C. until a clear solution formed. Phase B was charged to a separate vessel and mixed until components therein were homogeneous. Phase B was then slowly added to phase A under agitation with the Lightening mixer and mixing was continued for 10 further minutes. Thereafter, phase C was added to the combined phases A/B forming a white milky solution.

Specific Example 4: Oil Soluble Active in a Quaternized Liposome for Hair to Impart Shine

| Phase | Ingredient | % |
|---|---|---|
| A | Polyglyceryl-10 Dioleate/Polyglyceryl-10 Dilinoleate | 10.0 |
| A | Phenyltrimethicone | 10.0 |
| B | Water | 20.0 |
| B | Polyquaternium-10 | 1.0 |
| C | Water | 59.0 |

The specific oil soluble active in a quaternized liposome for hair to impart shine (Example 4) was produced as follows. The manufacturing process was started by stirring phase A with a Lightening mixer until the phase turned homogeneous. Phase B was charged to a separate vessel and mixed until components therein were homogeneous. Phase B was then slowly added to phase A under agitation with the Lightening mixer and mixing was continued for 10 further minutes. Thereafter, phase C was slowly added to the combined phases A/B forming a white milky solution.

Example 11

The following composition is an anti-acne lotion whose active agent is salicylic acid. See the Table below for the components of the lotion.

| Phase | Trade Name | % |
|---|---|---|
| A | Water | 50.5 |
| A | Butylene Glycol | 10.0 |
| B | Hydroxyethylcellulose | 2.0 |
| C | Hydrogenated Polydecene | 10.0 |
|   | Cyclopentasiloxane | 15.0 |
|   | GMS/PEG-100 Stearate | 2.5 |
| D | Polyglyceryl-10 Dioleate/Salicylic Acid/C12-14 Alkyl Benzoate/Water | 10.0 |
|   |   | 100.0 |

The lotion was prepared by the following manufacturing process. The process was started by charging a vessel with phase A and stirring with a homogenizing mixer for 2 minutes. Phase B was slowly added at room temperature and with stirring to the vessel containing phase A. Mixing was continued for at least 10 minutes until phase B was completely dispersed and free of lumps. The combined phases A/B were then heated at 75-80° C. with homogenizing mixing.

Phase C was charged to a separate vessel and heated to 75-85° C. under mixing. When all phases reached the 75-80° C., phase C was added into phases A/B under homogenizing mixing and continued for 10 minutes at a medium mixing speed. Cooling to 60° C. was followed by transfer of the batch (phases A/B/C) to a vessel having a sweep mixer and mixing continued at slow speed till temperature bottomed to 35° C. Thereupon, pH of the batch was adjusted to 3.5-4.0 using 40% citric acid/water solution as acidifying agent while slowly sweep mixing. The batch was then transferred for storage to a sterile container.

Example 12

The following composition is a high shine hair conditioner whose active agent are phenyltrimethicone and Polyquaternium-10. See the Table below for the components of the conditioner.

| Phase | Trade Name | % |
|---|---|---|
| A | Water | 58.5 |
| A | Butylene Glycol | 10.0 |
| B | Hydroxyethylcellulose | 2.0 |
| C | Cyclopentasiloxane | 15.0 |
|   | GMS/PEG-100 Stearate | 2.5 |
|   | Cetearyl Alcohol | 2.0 |
| D | Polyglyceryl-10 Dioleate/Phenyltrimethicone/Polyquaternium-10/Water | 10.0 |
|   |   | 100.0 |

The conditioner was prepared by the following manufacturing process. The process was started by charging a vessel with phase A and stirring with a homogenizing mixer for 2 minutes. Phase B was slowly added at room temperature and with stirring to the vessel containing phase A. Mixing was continued for at least 10 minutes until phase B was completely dispersed and free of lumps. The combined phases A/B were then heated at 75-80° C. with homogenizing mixing.

Phase C was charged to a separate vessel and heated to 75-85° C. under mixing. When all phases reached the 75-80° C., phase C was added into phases A/B under homogenizing mixing and continued for 10 minutes at a medium mixing speed. Cooling to 60° C. was followed by transfer of the batch (phases A/B/C) to a vessel having a sweep mixer and mixing continued at slow speed till temperature bottomed to 35° C. Thereupon, pH of the batch was adjusted to 5.0-5.5 using 40% citric acid/water solution as acidifying agent while slowly sweep mixing. The batch was then transferred for storage to a sterile container.

While the present compositions and methods have been described with reference to the specific variations thereof, it should be understood by those skilled in the art that various changes may be made and equivalents may be substituted without departing from the true spirit and scope of the compositions and methods described herein. In addition, many modifications may be made to adapt a particular situation, material, composition of matter, process, process step or steps, to the objective, spirit and scope of the compounds and methods described herein. All patents and publications cited above are hereby incorporated by reference.

What is claimed is:

1. A liposome comprising liposome structuring amounts of polyglyceryl-10 dioleate and polyglyceryl-10 dilinoleate in a weight ratio of 100:1 to 10:1.

2. The composition according to claim 1 wherein the polyglyceryl-10 dioleate and polyglyceryl-10 dilinoleate are present in a weight ratio of 100:8 to 100:4.

3. A composition comprising:
    a) liposomes comprising:
        (i) liposome structuring amounts of polyglyceryl-10 dioleate and polyglyceryl-10 dilinoleate in a weight ratio of 100:1 to 10:1; and
        (ii) an active material delivering consumer benefits incorporated into a lipid or aqueous phase of the liposome, the active material being selected from the group consisting of fragrances, flavors, sunscreen agents, emollients, hair conditioning agents, alpha and beta hydroxy acids, retinoids, proteins, peptides, plant actives, benzoyl peroxide, skin whitening agents, exfoliating agents and mixtures thereof; and
    b) an aqueous carrier suspending the liposomes therein.

4. The composition according to claim 3 wherein the fragrance is selected from the group consisting of amyl salicylate, carvacrol, cymene, dihydroeugenol, eugenol, hexyl eugenol, hexyl salicylate, isoeugenol, methyl eugenol, methyl isoeugenol, methyl salicylate, tert butyl cresol, thymol, vanillin, cedrene, cineole, citral, geranial, neral, citronellal, citronellol, eucalyptol, paradihydrolinalool, dihydromyrcenol, farnesol, geraniol, hexyl cinnamaldehyde, hydroxycitronallol, hydroxycitronellal, isocitral, limonene, linalool, longifolene, menthol, nerol, nerolidiol, α-pinene, phellendrene, terpinene, terpineol, tetrahydromyrcenol and mixtures thereof.

5. The composition according to claim 3 wherein the sunscreen agents are selected from the group consisting of 2-ethylhexyl p-methoxycinnamate, 4,4'-t-butyl methoxydibenzoylmethane, octylsalicylate, tetraphthalylidene dicamphor sulfonic acid, benzophenone-3, microfine titanium dioxide, microfine zinc oxide and mixtures thereof.

6. The composition according to claim 3 wherein the liposomes have a Dynamic Light Scattering value between 1 and 1000 nm.

7. The composition according to claim 3 wherein the liposomes have a Dynamic Light Scattering value between 5 and 200 nm.

8. A liposome composition comprising:
    liposomes comprising:
        liposome structuring amounts of polyglyceryl-10 dioleate and polyglycerol-10 dilinoleate in a weight ratio of 100:1 to 10:1; and
        a water soluble cationic material held within an interior aqueous medium of the liposomes present in an amount from 0.00001 to 30% by weight of the composition.

9. The composition according to claim 8 wherein the cationic material is a monomeric quat selected from the group consisting of mono-, di-, and tri-alkyl or aryl quats.

10. The composition according to claim 8 wherein the cationic material is selected from the group consisting of cetyltrimethylammonium chloride, cetyl pyridinium chloride, behenyltrimethylammonium methosulfate, benzyltrimethylammonium chloride, and oleoylmonomethyldihydrogenammonium chloride.

11. The composition according to claim 8 wherein the cationic material is a polymeric quat.

12. The composition according to claim 11 wherein the polymeric quat is a saccharide selected from the group consisting of guar hydroxypropyltrimethylammonium chloride, hydroxypropyltrimethylammonium hydrolyzed wheat protein, and hydroxypropyltrimethylammonium honey.

13. The composition according to claim 8 wherein the polyglyceryl-10 dioleate and polyglyceryl-10 dilinoleate are present in a weight ratio of 100:8 to 100:4.

14. The composition according to claim 8 wherein the liposomes have a Dynamic Light Scattering value between 5 and 200 nm.

* * * * *